(12) United States Patent
Barrett et al.

(10) Patent No.: US 11,141,515 B2
(45) Date of Patent: Oct. 12, 2021

(54) SYSTEM AND METHOD FOR DIALYZER EVALUATION

(71) Applicant: Fresenius Medical Care Holdings, Inc., Waltham, MA (US)

(72) Inventors: Louis LeeGrande Barrett, West Point, UT (US); Chih-Hu Ho, Farmington, UT (US); Eric Stroup, Midway, UT (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 0 days.

(21) Appl. No.: 16/943,794

(22) Filed: Jul. 30, 2020

(65) Prior Publication Data

US 2020/0353145 A1 Nov. 12, 2020

Related U.S. Application Data (63) Continuation of application No. 16/801,666, filed on Feb. 26, 2020, now Pat. No. 10,765,792, which is a
(Continued)

(51) Int. Cl.
*A61M 1/26* (2006.01)
*A61M 1/16* (2006.01)
*A61M 1/36* (2006.01)

(52) U.S. Cl.
CPC .......... *A61M 1/1692* (2013.01); *A61M 1/267* (2014.02); *A61M 1/361* (2014.02);
(Continued)

(58) Field of Classification Search
CPC .... A61M 1/1692; A61M 1/267; A61M 1/361; A61M 1/3612; A61M 1/3663;
(Continued)

(56) References Cited

U.S. PATENT DOCUMENTS 3,763,376 A * 10/1973 Diamanti ............ A61M 1/1692
250/565
4,140,633 A 2/1979 Goldhaber
(Continued)

FOREIGN PATENT DOCUMENTS

WO  WO 2011/000086 A1  1/2011

OTHER PUBLICATIONS

International Patent Application No. PCT/US2018/050797, Search Report (dated Nov. 14, 2018).
(Continued)

*Primary Examiner* — David J Bolduc
(74) *Attorney, Agent, or Firm* — Leydig, Voit & Mayer, Ltd.

(57) ABSTRACT

Embodiments of the disclosure provide a method for evaluating dialyzers used in different medical applications (e.g., hemodialysis). Red blood cell volume lost in a dialyzer is monitored by obtaining blood flowrate measurements and hematocrit measurements at input ports and output ports of the dialyzer. The flowrate and hematocrit measurements are used to determine an accumulation of red cell blood volume in the dialyzer. The measurements may be obtained in a lab environment with an in-vitro blood source or may be obtained in a clinical setting with an in-vivo blood source from a patient.

22 Claims, 6 Drawing Sheets

Related U.S. Application Data continuation of application No. 15/720,642, filed on Sep. 29, 2017, now Pat. No. 10,625,011.

(52) U.S. Cl.
CPC ......... *A61M 1/3612* (2014.02); *A61M 1/3663* (2013.01); *A61M 2205/3306* (2013.01); *A61M 2205/3334* (2013.01); *A61M 2205/3386* (2013.01); *A61M 2205/702* (2013.01); *A61M 2205/707* (2013.01); *A61M 2230/207* (2013.01)

(58) Field of Classification Search
CPC .. A61M 2205/3306; A61M 2205/3334; A61M 2205/3386; A61M 2205/702; A61M 2230/207
See application file for complete search history.

(56) References Cited

U.S. PATENT DOCUMENTS

| | | | |
|---|---|---|---|
| 5,372,136 A | 12/1994 | Steuer et al. | |
| 5,709,670 A | 1/1998 | Vancaillie et al. | |
| 5,928,180 A | 7/1999 | Krivitski et al. | |
| 6,689,083 B1 * | 2/2004 | Gelfand | A61M 1/3609 604/5.04 |
| 7,473,238 B2 | 1/2009 | Brugger et al. | |
| 2001/0020122 A1 | 9/2001 | Steuer et al. | |
| 2002/0085951 A1 * | 7/2002 | Gelfand | A61M 1/34 422/44 |
| 2003/0130570 A1 | 7/2003 | Krivitski et al. | |
| 2004/0129616 A1 | 7/2004 | Mori et al. | |
| 2005/0131332 A1 * | 6/2005 | Kelly | A61M 1/16 604/4.01 |
| 2005/0203493 A1 | 9/2005 | Kuroda et al. | |
| 2005/0284815 A1 | 12/2005 | Sparks et al. | |
| 2008/0067132 A1 * | 3/2008 | Ross | A61B 5/0261 210/739 |
| 2008/0103427 A1 | 5/2008 | Toyoda et al. | |
| 2010/0113891 A1 | 5/2010 | Barrett et al. | |
| 2011/0139690 A1 * | 6/2011 | Akita | G01N 21/59 210/96.1 |
| 2011/0144459 A1 * | 6/2011 | Akita | A61M 1/1609 600/310 |
| 2012/0154789 A1 | 6/2012 | Barrett et al. | |
| 2013/0020237 A1 * | 1/2013 | Wilt | A61M 1/301 210/85 |
| 2014/0199193 A1 * | 7/2014 | Wilt | A61M 1/3609 417/477.2 |
| 2014/0299544 A1 * | 10/2014 | Wilt | F04B 43/14 210/646 |
| 2015/0238672 A1 * | 8/2015 | Barrett | G01N 21/05 356/40 |
| 2016/0058933 A1 * | 3/2016 | Ballantyne | G05B 15/02 210/85 |
| 2016/0367155 A1 | 12/2016 | Barrett et al. | |
| 2017/0326282 A1 * | 11/2017 | Wilt | A61M 1/3638 |
| 2018/0236152 A1 * | 8/2018 | Khair | A61M 1/3639 |
| 2018/0361051 A1 * | 12/2018 | Kopperschmidt | A61M 1/3656 |

OTHER PUBLICATIONS

European Patent Application No. 18 860 284.1, Search Report (dated May 27, 2021).
U.S. Appl. No. 15/720,642, filed Sep. 29, 2017.
U.S. Appl. No. 16/801,666, filed Feb. 26, 2020.

\* cited by examiner

SYSTEM AND METHOD FOR DIALYZER EVALUATION

CROSS-REFERENCE TO RELATED APPLICATIONS

This patent application is a continuation of copending U.S. patent application Ser. No. 16/801,666, filed Feb. 26, 2020, which is a continuation of U.S. patent application Ser. No. 15/720,642, filed Sep. 29, 2017, now U.S. Pat. No. 10,625,011. The aforementioned patent applications are incorporated by reference herein in their entireties.

BACKGROUND

Patients with kidney failure or partial kidney failure typically undergo hemodialysis treatment, often at a hemodialysis treatment center or clinic. When healthy, kidneys maintain the body's internal equilibrium of water and minerals (e.g., sodium, potassium, chloride, calcium, phosphorous, magnesium, and sulfate). The kidneys also function as part of the endocrine system to produce the hormone erythropoietin as well as other hormones. Hemodialysis is an imperfect treatment to replace kidney function, in part, because it does not correct the endocrine functions of the kidney.

In hemodialysis, blood is taken from a patient through an intake needle (or catheter) which draws blood from an artery located in a specific accepted access location (arm, thigh, subclavian, etc.). The drawn blood is pumped through extracorporeal tubing via a peristaltic pump, and then through a special filter termed a "dialyzer." The dialyzer is intended to remove unwanted toxins such as blood urea, nitrogen, potassium, and excess water from the blood. As the blood passes through the dialyzer, it travels in straw-like tubes which serve as semi-permeable membrane passageways for the uncleaned blood. Fresh dialysate liquid, which is a solution of chemicals and water, flows through the dialyzer in the direction opposite the blood flow. As the dialysate flows through the dialyzer, it surrounds the straw-like membranes in the dialyzer. These membranes feature small holes which are large enough to pass liquid and liquid based impurities—but are not large enough to pass red blood cells. The fresh dialysate collects excess impurities passing through the straw-like tubes by diffusion, and also collects excess water through an ultrafiltration process due to a pressure drop across the membranes. During this process, the red cell volume is preserved inside the straw-like tubes and recirculated back into the body. The used dialysate exits the dialyzer with the excess fluids and toxins via an output tube, thus cleansing the blood and red cell volume flowing through the dialyzer. The dialyzed blood then flows out of the dialyzer via tubing and a needle (or catheter) back into the patient. Sometimes, a heparin drip or pump is provided along the extracorporeal blood flow loop in order to prevent red cell clotting during the hemodialysis process. Several liters of excess fluid can be removed during a typical multi-hour treatment session. In the U.S., a chronic patient will normally undergo hemodialysis treatment in a dialysis center three times per week, either on Monday-Wednesday-Friday schedule or a Tuesday-Thursday-Saturday schedule. These in-center treatments are typically completed over 3 to 4 hours with blood flow rates typically above 300 ml/minute. In other countries, the flow rates and time for treatment are lower and longer, respectively.

Hemodialysis has an acute impact on the fluid balance of the body due in part to the rapid change in circulating blood volume. When the dialysis fluid removal rate is more rapid than the plasma refilling rate of the stored plasma held by the internal tissue of the body, intravascular blood volume decreases. The resulting imbalance has been linked to complications similar to conventional blood loss such as hypotension, loss of consciousness, headaches, vomiting, dizziness and cramps experienced by the patient, both during and after dialysis treatments. Continuous quantitative measurement of parameters relating to the processing of the blood volume (in real-time) during hemodialysis can reduce the chance of dialysis-induced hypotension, and otherwise optimize dialysis therapy regimens by controlling fluid balance and aiding in achieving the target dry weight for the patient.

The effectiveness of the dialyzer in filtering the patient's blood directly affects the patient outcome. Dialyzers are rated by how effective they are at removing the toxins in the patient's blood. This rating is termed a dialyzer's "Clearance," which is a rate at which blood passes through the dialyzer, expressed as a volume of blood passing through the dialyzer per unit of time.

SUMMARY

An embodiment of the disclosure provides a system for evaluating a dialyzer. The system includes: a blood source; a first portion of tubing, configured to connect the blood source to an input of the dialyzer; a second portion of tubing, configured to connect to an output of the dialyzer; a pump, configured to pump blood from the blood source through the first portion of tubing into the dialyzer, and out of the dialyzer into the second portion of tubing; and a first blood chamber or port, disposed along the first portion of tubing, and a second blood chamber or port, disposed along the second portion of tubing, wherein the first blood chamber or port and the second blood chamber or port are configured to facilitate hematocrit measurement.

Another embodiment of the disclosure provides a method for evaluating a dialyzer using a dialyzer test system connected to a dialyzer. The method includes: circulating, using a pump of the dialyzer test system, blood from a blood source through the dialyzer; and determining, using the dialyzer test system, a red blood volume loss corresponding to the dialyzer, wherein determining the red blood volume loss includes: (a) determining a blood flowrate corresponding to an input side of the dialyzer via a calibrated pumping rate of the pump or an input flowmeter of the dialyzer test system; (b) determining a hematocrit corresponding to the input side of the dialyzer via a first sensor assembly of the dialyzer test system attached to a first blood chamber of the dialyzer test system, wherein the first sensor clip assembly and the first blood chamber are disposed on the input side of the dialyzer; (c) determining a blood flowrate corresponding to an output side of the dialyzer via an ultrafiltration rate and the blood flowrate corresponding to an input side of the dialyzer; and (d) determining a hematocrit corresponding to the output side of the dialyzer via a second sensor clip assembly of the dialyzer test system attached to a second blood chamber of the dialyzer test system, wherein the second sensor clip assembly and the second blood chamber are disposed on the output side of the dialyzer.

Yet another embodiment of the disclosure provides a method for evaluating a dialyzer using a dialyzer test system connected to a dialyzer. The method includes: circulating, using a pump of the dialyzer test system, blood from a blood source through the dialyzer; and determining, using the dialyzer test system, a red blood volume loss corresponding to the dialyzer, wherein determining the red blood volume loss includes: (a) determining a blood flowrate corresponding to an input side of the dialyzer by via a calibrated pumping rate of the pump or an input flowmeter of the dialyzer test system; (b) determining a hematocrit corresponding to the input side of the dialyzer based on blood drawn from a first port of the dialyzer test system, wherein the first port is on the input side of the dialyzer; (c) determining a blood flowrate corresponding to an output side of the dialyzer via an ultrafiltration rate and the blood flowrate corresponding to an input side of the dialyzer; and (d) determining a hematocrit corresponding to the output side of the dialyzer based on blood drawn from a second port of the dialyzer test system, wherein the second port is on the input side of the dialyzer.

DETAILED DESCRIPTION

Dialyzers can accumulate red cells in mechanical corners and pockets within the dialyzer filter fibers. When red blood cells stagnate within the dialyzer filter fibers instead of being rejuvenated by circulation through the body, heart, and lungs, they tend to deteriorate over time and coagulate, that is, bond to each other forming a clot. Blood clots during dialysis represent blood loss from the overall body blood volume of red cells. Increased clotting or blood coagulation within the dialyzer can render the dialyzer increasingly ineffective as the treatment continues and ultimately restrict the dialysis circuit flow rate through parts of the dialyzer.

In an exemplary embodiment, the disclosure provides for quantifying actual red cell loss as a result of using a particular dialyzer. As blood passes through the small fibers of the dialyzer, the incidental movement and collisions of the red cells with the extended lengths of the internal straw-like fibers can cause red cells to lodge within the dialyzer. Heparin use is limited because, while it tends to minimize the lodging and clotting of red cells within the dialyzer, it also reduces the patient's short-term ability to stop bleeding—whether externally or internally—for several hours. A practical dose of Heparin for patient safety may not be sufficient to prevent clotting from occurring within the hundreds of cumulative feet of internal dialyzer fibers.

In services such as Continual Renal Replacement Therapy (CRRT), where slow-speed dialysis in the Intensive Care Unit (ICU) environment is at times administered, clotting in the dialyzer is common. When clotting occurs, replacement of the dialyzer and tubing set on the CRRT device is often performed, and this results in the loss of the residual blood discarded in the dialyzer and tubing set from the patient. Incidental loss of this blood volume in discarded disposables can, in some cases, present a negative effect on the patient's overall blood volume level.

Exemplary embodiments of the disclosure use measured or other available information to calculate and quantify the loss of red cell volume due to these cells either clotting or lodging in the dialyzer over time. This quantified loss of red cell volume can potentially be used as another qualifier for dialyzer effectiveness and quality of dialyzer filters.

Exemplary embodiments of the disclosure provide a method for quantitatively evaluating the clotting rate of a dialyzer and using the quantitative evaluation as a potential rating value for dialyzer efficiency. A family of dialyzers with low loss of red blood cells per a given treatment time may be considered better than a different family of dialyzers with a much shorter clotting time, even when both families of dialyzers have the same dialyzer clearance rating.

Figure 1:
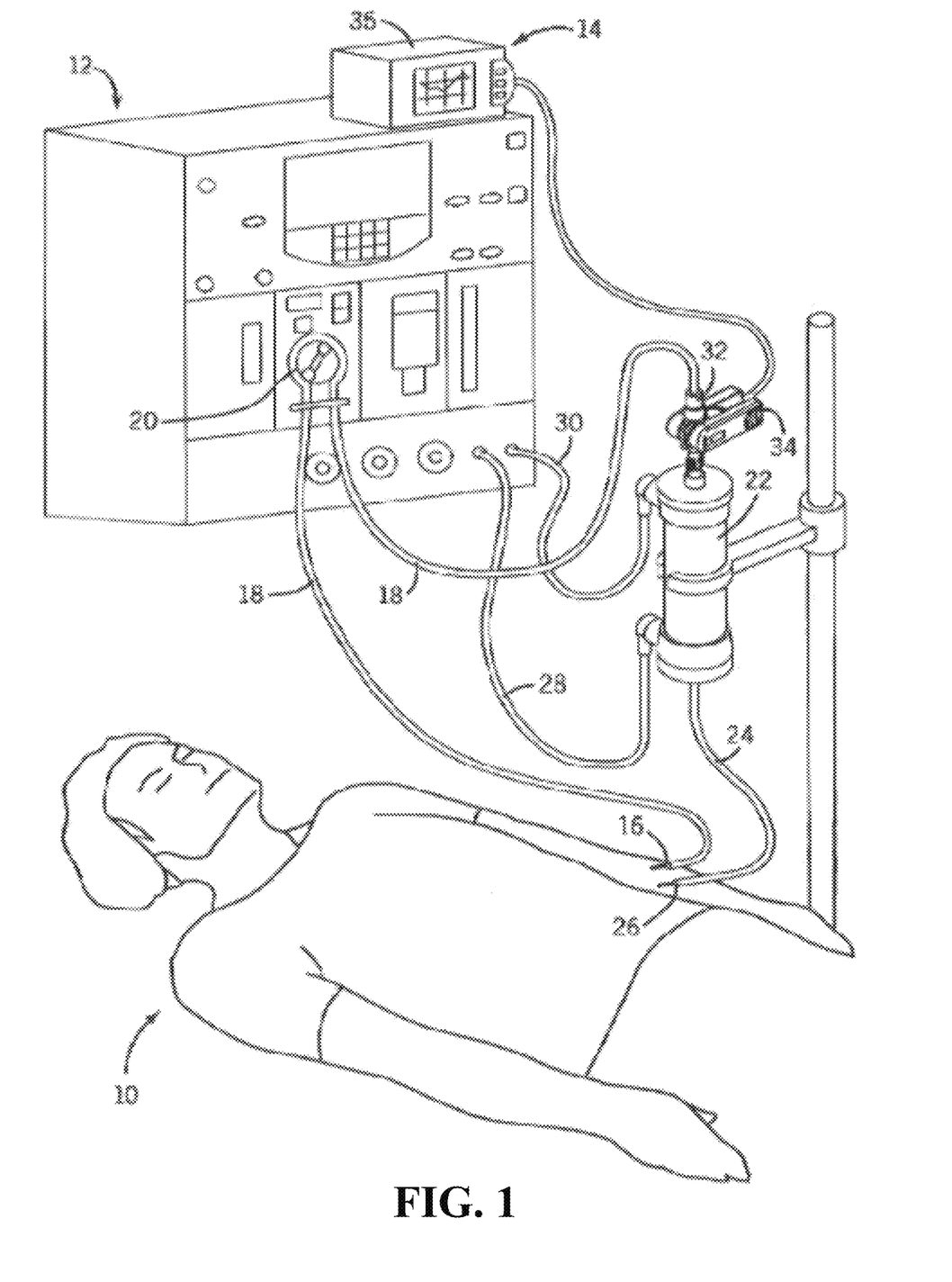
FIG. 1 is a perspective view of a typical patient undergoing hemodialysis treatment with a non-invasive, optical blood monitor monitoring the patient's blood in real-time as it passes through extracorporeal tubing in the hemodialysis system.

FIG. 1 is a perspective view of an exemplary patient undergoing hemodialysis treatment with a non-invasive, optical blood monitor monitoring the patient's blood in real-time as it passes through extracorporeal tubing in the hemodialysis system. The environment illustrated in FIG. 1 is usable with exemplary embodiments of the present disclosure. Further, it will be appreciated that the environment shown in FIG. 1 is merely exemplary, and that the principles discussed herein with respect to exemplary embodiments of the present disclosure may be implemented in other environments as well.

FIG. 1 illustrates a patient 10 undergoing hemodialysis treatment using a conventional hemodialysis system 12, as well as a non-invasive, optical blood monitor 14. A typical hemodialysis clinic will have several hemodialysis systems 12 for treating patients on a Monday-Wednesday-Friday schedule or a Tuesday-Thursday-Saturday schedule. While the invention is not limited to the number of hemodialysis systems located at a clinic, or the specific type of hemodialysis system, the general operation of the hemodialysis system 12 is helpful for understanding the environment in which the invention is intended to operate.

An input needle or catheter 16 is inserted into an access site of the patient 10, such as in the arm, and is connected to extracorporeal tubing 18 that leads to a peristaltic pump 20 and then to a dialyzer or blood filter 22. The dialyzer 22 removes toxins and excess fluid from the patient's blood. The dialyzed red cell blood volume is returned from the dialyzer 22 through extracorporeal tubing 24 and return needle or catheter 26. In some parts of the world (primarily the United States), the extracorporeal blood flow may additionally receive a heparin drip to prevent clotting. The excess fluids and toxins are removed by clean dialysate liquid, which is supplied to the dialyzer 22 via tube 28 and removed for disposal via tube 30. A typical hemodialysis treatment session takes about 3 to 5 hours in the United States.

In the exemplary environment depicted in FIG. 1, the optical blood monitor 14 includes a blood chamber 32, an optical blood sensor assembly 34, and a controller 35. The blood chamber 32 is preferably located in line with the extracorporeal tubing 18 upstream of the dialyzer 22. Blood from the peristaltic pump 20 flows through the tubing 18 into the blood chamber 32. The preferred sensor assembly 34 includes LED photo emitters that emit light optical wavelengths, for example, at substantially 810 nm, which is isobestic for red blood cell hemoglobin. The blood chamber 32 includes lenses so that the emitters and detectors of the sensor assembly 34 can view the blood flowing through the blood chamber 32, and determine the patient's real-time hematocrit value using ratiometric techniques generally known in the prior art.

Figure 2:
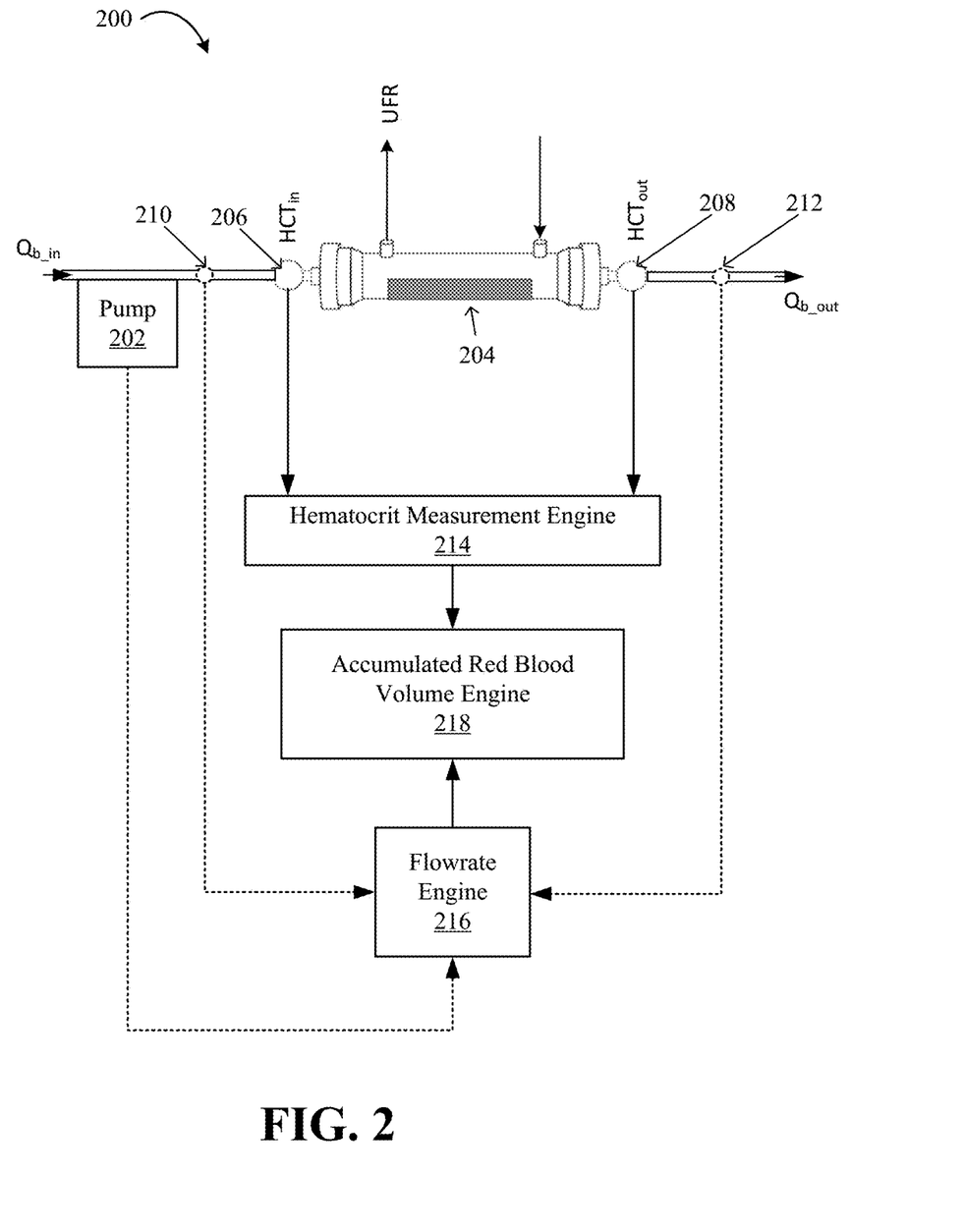
FIG. 2 illustrates an exemplary system for determining the accumulated red blood volume lost in a dialyzer per unit time according to some embodiments of the disclosure.

FIG. 2 illustrates an exemplary system 200 that may be used to determine dialyzer efficiency by monitoring accumulated red blood volume retained in a dialyzer 204, according to some embodiments of the disclosure. The system 200 includes a hematocrit measurement engine 214, a flowrate measurement engine 216, and an accumulated red blood volume engine 218.

Figure 3:
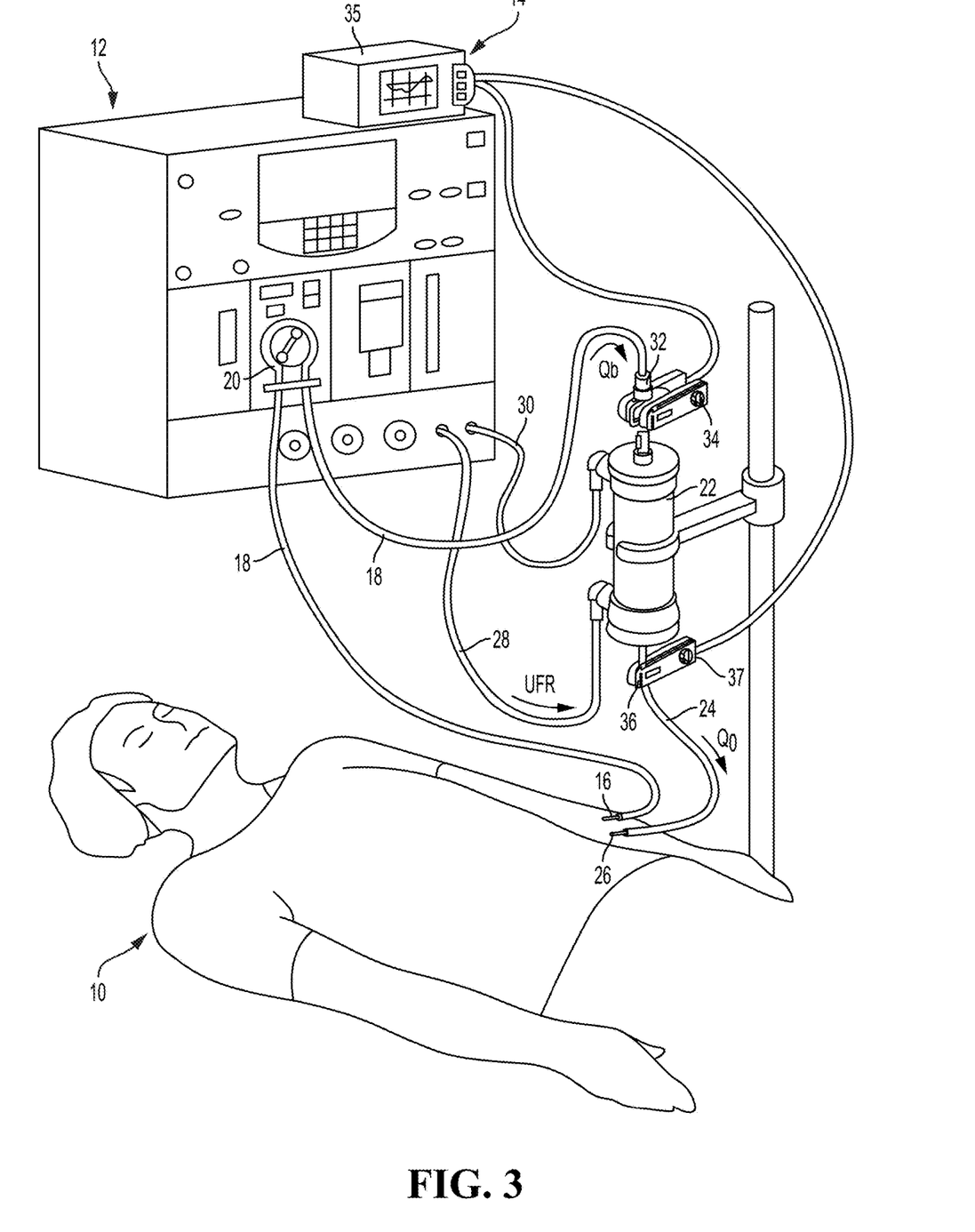
FIG. 3 illustrates a view of a patient undergoing hemodialysis treatment with a system configuration that may be used to determine accumulated red blood volume lost per unit time according to some embodiments of the disclosure.
Figure 4:
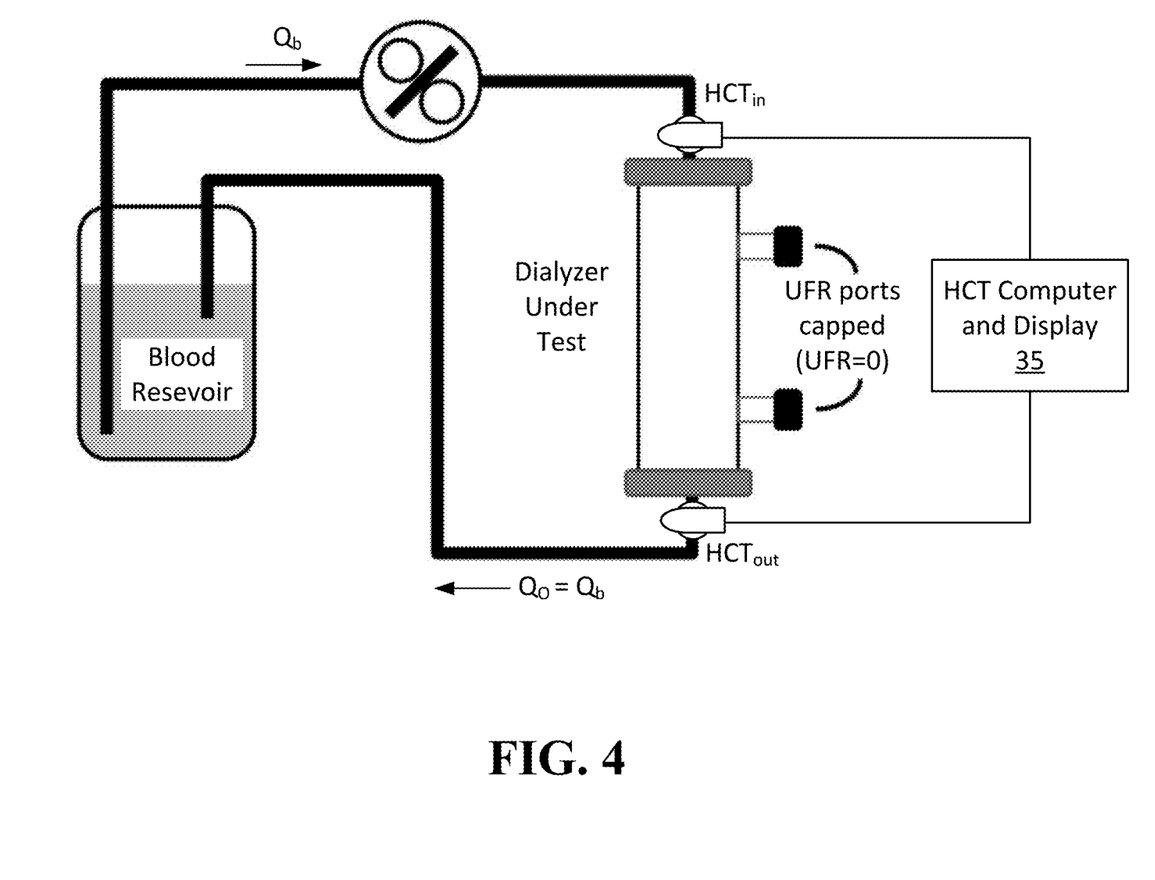
FIG. 4 illustrates another system configuration for determining accumulated red blood volume lost per unit time according to some embodiments of the disclosure.

The exemplary system 200 shows a generalized embodiment which may be incorporated in either the hemodialysis system 12 provided, as outlined in FIG. 3, or in a laboratory setting as shown in FIG. 4. In FIG. 3, the hematocrit measurement engine 214, the flowrate measurement engine 216, and the accumulated red blood volume engine 218 may be implemented in the hemodialysis system 12 and the non-invasive, optical blood monitor 14. In this configuration, the flowrate measurement engine 216 may be included in the hemodialysis system 12, the hematocrit measurement engine 214 included in the optical blood monitor 14, and the accumulated red blood volume engine 218 included in the optical blood monitor 14 and/or in the hemodialysis system 12. The hemodialysis system 12 and the optical blood monitor 14 can be communicably coupled to each other to realize the relationships provided in FIG. 2 for system 200, or the desired parameters can be measured independently with discrete calculations. The integrated configuration represents an embodiment of how a real-time efficiency measurement could be made of the dialyzer in use on a per-treatment basis.

For an integrated embodiment, the hematocrit measurement engine 214, the flowrate measurement engine 216, and the accumulated red blood volume engine 218 correspond to hardware that includes one or more processors, for example, microprocessors or microcontrollers. The hardware also includes a non-transitory computer-readable medium for temporary and/or permanent storage, for example, a read-only memory (ROM), a random access memory (RAM), a flash memory, and other computer memories and storage. Additionally, the hematocrit measurement engine 214 may utilize one or more optical blood sensor assemblies, for example, optical blood sensor assembly 34, to measure hematocrit values at both main blood flow ports of the dialyzer 204. The accumulated red blood volume engine 218 may be a computing device, for example, the controller 35, that utilizes a processor and storage to determine the hematocrit values of the dialyzer 204, read the blood flowrate entering the dialyzer 204 from the processor in the dialysis machine 12, read the ultra-filtration rate of the dialysis machine 12 and then calculate the accumulated red blood volume lost in the dialyzer 204.

In the system 200 of FIG. 2, as applied to FIG. 3, blood flows into an input port of the dialyzer 204 at a blood flowrate $Q_{b\_in}$. The blood flowrate is determined by the pump 202, which may be peristaltic pump 20, which is part of the dialysis machine 12 of FIG. 3. In the treatment setting of FIG. 3, blood enters the dialyzer 204, undergoes a filtration process, and filtered blood flows out of an output port of the dialyzer 204 at a blood flowrate $Q_{b\_out}$. The difference between the blood flowrate at the input port of the dialyzer 204 and the blood flowrate at the output port of the dialyzer 204 is denoted in FIG. 2 as ultra-filtration rate (UFR). In the treatment setting of FIG. 3, the $Q_{b\_out}$ rate is the difference of the $Q_{b\_in}$ rate minus the UFR. The pumps on the dialysis machine 12 are calibrated, and these calibrated values are readily available during measurements. These rates can be arbitrary, but remain the same throughout the measurements.

Multiple methods may be used to determine the flowrates $Q_{b\_in}$ and $Q_{b\_out}$. As shown in FIG. 2, in one embodiment, a flowmeter 210 is provisioned in the extracorporeal tubing to measure $Q_{b\_in}$. The measurements from the flowmeter 210 may be provided to the flowrate engine 216. In a similar fashion, the flowmeter 212 may be provisioned in the extracorporeal tubing to measure $Q_{b\_out}$.

In another exemplary embodiment, for a laboratory environment for evaluating dialyzers (FIG. 4), the flowmeter 210 may or may not be provided, depending on whether $Q_{b\_in}$ is determined from a calibrated pumping rate of the pump 202. The pump 202 may operate at a specific number of rotations per minute, which may be matched to a commanded flowrate of blood entering the dialyzer 204. The pump 202 may provide the number of rotations per minute to the flowrate engine 216, which then determines $Q_{b\_in}$ from the number of rotations per minute.

In the laboratory environment, the ports for dialysate flow can be plugged such that a UFR is zero. UFR may not be required in a laboratory setting where patients are not treated. The laboratory environment may produce a base red cell efficiency value through time testing. Another study may be performed to evaluate whether the efficiency of a given dialyzer is affected by the pulling of fluids, and hence red cells, against the straw fiber walls under osmality of dialysate flow versus the laboratory condition with no dialysate flow. Nonetheless, the mass balance of the equations remains the same.

In addition to determining flowrates, the system 200 also determines hematocrit at the input port of the dialyzer 204 ($HCT_{in}$) and the output port of the dialyzer 204 ($HCT_{out}$). In one embodiment, a ratiometric technique, as disclosed in U.S. Pat. No. 5,372,136 entitled, "System and Method for Non-Invasive Hematocrit Monitoring," which is incorporated by reference in its entirety, can be used to determine hematocrit values at locations 206 and 208 in FIG. 2.

The method of measuring hematocrit can be varied. Simultaneous or near simultaneous (within minutes) samples of blood from before and after the dialyzer (206 and 208 in FIG. 2) can be taken, placed in capulary tubes and then spun on a calibrated centrifuge, per accepted medical practices. The ratio of red cell length in the tube to the total sample length will yield hematocrit. In another embodiment, the samples can be measured on a cell counter instead of spinning them in capulary tubes. In another embodiment, the samples may be measured with a hemoglobin measurement device, such as, any hemoglobin measurement system by HemoCue®. The hemoglobin measurements may then be multiplied by 2.94 to obtain equivalent hematocrits. In other embodiments, non-invasive (not requiring the pulling of samples) hematocrit measurements, for example, measurements made with the Crit-Line® system, may be used to obtain hematocrit values.

The accumulated red blood volume engine 218 receives hematocrit measurements from the hematocrit measurement engine 214 and receives flowrate measurements from the flowrate engine 216. Using the hematocrit and the flowrate measurements, the accumulated red blood volume engine 218 determines the red cell blood volume loss (or red blood volume loss) in the dialyzer 204. The amount of red blood volume loss in the dialyzer 204 is determined by accumulating over time the difference between red blood volume flowing into the dialyzer 204 and red blood volume flowing out of the dialyzer 204.

Red blood volume flowing into the dialyzer 204 is related to the hematocrit at the input port of the dialyzer 204 and the blood flowrate at the input port of the dialyzer 204 through Eq. 1.

$$HCT_{in} = \frac{RBV_{in}}{Q_{b\_in}} \qquad \text{Eq. 1}$$

Red blood volume flowing out of the dialyzer 204 is related to the hematocrit at the output port of the dialyzer 204 and the filtered blood flowrate at the output port of the dialyzer 204 through Eq. 2.

$$HCT_{out} = \frac{RBV_{out}}{Q_{b\_out}} \qquad \text{Eq. 2}$$

The filtered blood flowrate $Q_{b\_out}$ is related to the Ultra-Filtration Rate (UFR) and the input blood flowrate $Q_{b\_in}$ through Eq. 3.

$$Q_{b\_out} = Q_{b\_in} - UFR \qquad \text{Eq. 3}$$

Embodiments of the disclosure use the hematocrit monitoring engine 214 to measure the HCT of the blood entering the dialyzer 204 and then the HCT blood exiting the dialyzer 204. Due to the nature of the dialyzer 204, no red blood cells are lost across dialyzer membranes within the dialyzer 204—only fluid, for example, urea, passes through into the waste collecting dialysate. Since red blood cells do not cross the dialyzer membranes into the waste, mass balance analysis of the red blood cell volume over time may be used to determine the red blood cell loss in the dialyzer 204, based on the input and output dialysis measurements of the dialyzer 204.

A difference ΔR between red blood volume flowing into the dialyzer 204 and red blood volume flowing out of the dialyzer 204 may be defined according to Eq. 4.

$$\Delta R = RBV_{in} - RBV_{out} \qquad \text{Eq. 4}$$

Combining Eq. 1 through Eq. 4 yields Eq. 5.

$$\Delta R = HCT_{in} \times Q_{b\_in} - HCT_{out} \times (Q_{b\_in} - UFR) \qquad \text{Eq. 5}$$

The accumulated red blood volume engine 218 determines ΔR using relationships shown in Eq. 1 through Eq. 5, depending on what information it receives from the hematocrit measurement engine 214 and flowrate engine 216. Note that in FIG. 2, the dotted lines represent potential alternative inputs for determining flowrate, some or all of which may be used in different exemplary embodiments. For example, the blood flowrate at the input of the dialyzer 204 is desired, but this flowrate can be determined from either the calibrated pump 202 or the flowmeter 210, thus one of these measurement paths may be active and the other inactive. From Eq. 5, if the filtered blood flowrate at the output of the dialyzer 204 is unavailable (the usual circumstance), then the calibrated UFR may be used to determine ΔR.

After determining ΔR, the accumulated red blood volume engine 218 continually combines historical values of ΔR to determine the amount of red blood volume loss in the dialyzer 204 over the designated period of time. During dialysis, the amount of red blood volume loss in the dialyzer 204 over the period of time represents an active clotting within the dialyzer.

Figure 5:
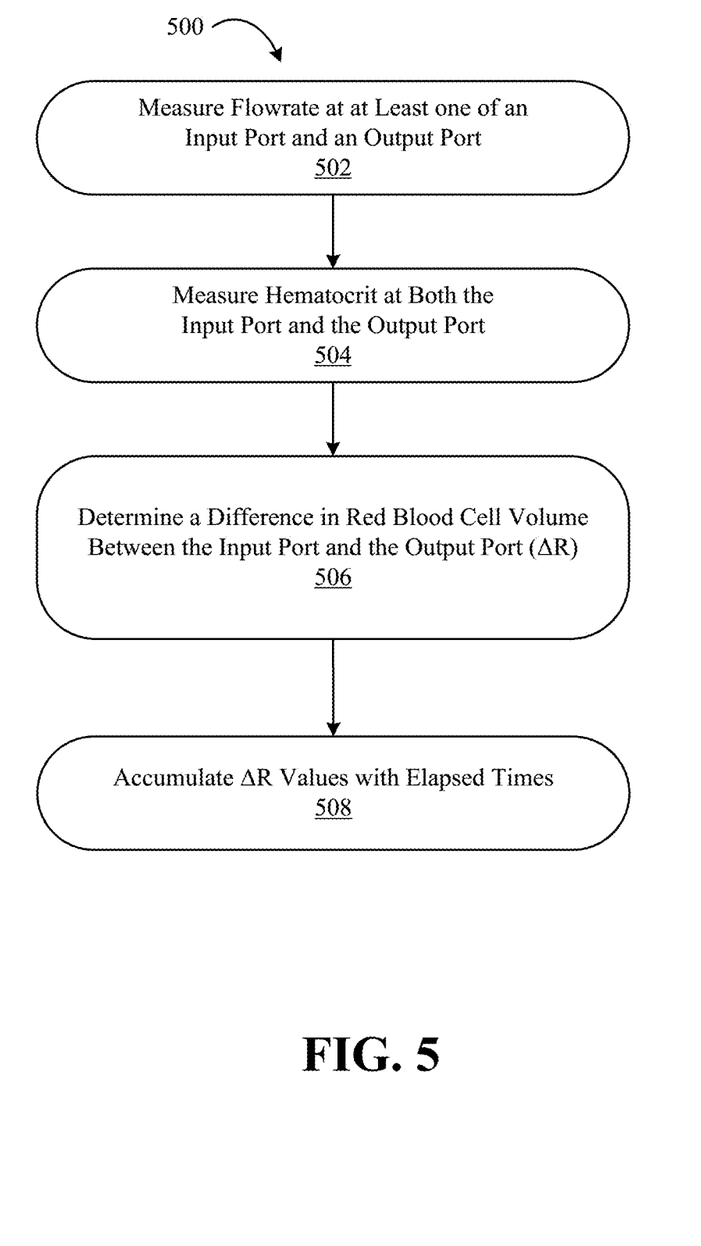
FIG. 5 illustrates a process of determining accumulated red blood volume lost per unit time according to some embodiments of the disclosure.

FIG. 5 illustrates a process 500 for determining accumulated red blood volume in a dialyzer, according to some embodiments included in the disclosure. At step 502, the system 200 measures flowrate at at least one of the input port or the output port of the dialyzer 204. From Eq. 3, blood flowrate at the input port of the dialyzer 204 and filtered blood flowrate at the output port of the dialyzer 204 are related though the UFR. If the input flow rate is measured at step 502, either the output flow rate is measured directly with a flow meter 212 or the output flow rate is calculated by subtracting the UFR from the input flow rate per Eq. 3. If the output flow rate is measured at step 502, either the input flow rate is measured directly with a flow meter 210, or the input flow rate is calculated by subtracting the UFR from the input flow rate per Eq. 3. As provided in the laboratory environment of FIG. 4, the UFR may be 0 in some embodiments, and as such, the input flowrate and the output flowrate are equal.

At step 504, the system 200 measures hematocrit at both the input port and the output port of the dialyzer 204. Using techniques already described, $HCT_{in}$ and $HCT_{out}$ are measured. Eq. 1 and Eq. 2 relate $HCT_{in}$ and $HCT_{out}$ to the flowrates obtained at step 502.

In a fully functional new dialyzer, mass balance shows that ΔR is zero at time=$t_0$. At step 506, the system 200 determines a change in red blood cell volume between the input port and the output port of the dialyzer 204 (ΔR at time=$t_n$). Using the flowrates at step 502 and the hematocrit measurements at step 504, the system 200 determines ΔR at time=$t_n$ with relationships provided in Eq. 4, Eq. 5, or substitutive equivalents of both, depending on which parameters are available to the system 200.

At step 508, the system 200 then determines an accumulated red blood cell volume remaining in the dialyzer. This may be done in multiple ways. In one embodiment, the accumulated red blood cell volume may be determined in a piecewise incremental fashion by multiplying the ΔR values by their respective time slices and summing discrete time period residual loss of blood in the dialyzer. In another embodiment, the accumulated red blood cell volume may be realized by determining a function for ΔR through mathematical regression and then integrating the resulting function over the time interval of interest.

Dialyzer efficiency may be evaluated according to embodiments of the disclosure. The accumulated red blood cell volume remaining in the dialyzer may be determined as a function of elapsed time, allowing dialyzers to be compared according to volume of red cells lost per unit time. By qualifying dialyzer efficiency in this manner, manufacturers and customers have a better understanding or idea of how red cells move through a dialyzer. The accumulated red blood cell volume may be stratified in categories, for example, good, fair, and poor. The categorization of dialyzers in this manner may help a manufacturer produce a dialyzer with new shells incorporating coatings that streamline how red cells move through the dialyzer. The categorization of dialyzers in this manner may also help healthcare providers select appropriate dialyzers for specific applications.

As described, dialyzer efficiency may be qualified according to volume of red cells lost per unit time. In an embodiment, the output of a system configuration for evaluating dialyzers, for example, the laboratory environment of FIG.

4 may display the accumulated red blood cell volume on the HCT computer and display 35. The displayed value of the accumulated red blood cell volume may allow a user to be able to compare a value of one dialyzer to another. In another embodiment, based on the value that the user obtains from the HCT computer and display 35, the user may determine that the dialyzer is in one of three categories, namely, good, fair, or poor. In another embodiment, the user may generate another type of rating for the dialyzer, for example, the user may use a pass-fail rating for the dialyzer.

In an exemplary implementation, the HCT computer and display 35 may determine that the dialyzer is in one of the three categories by comparing the accumulated red blood cell volume to two accumulated red blood cell volume thresholds. The two thresholds include a first threshold separating good dialyzers from fair dialyzers, and the second threshold separating fair dialyzers from poor dialyzers. The second threshold is higher than the first threshold, such that the accumulated red blood cell volume increases on on the continuum of good, fair, and poor. The HCT computer and display 35 may compare accumulated red blood cell volume obtained at step 508 with the first and the second thresholds to determine whether the dialyzer under test is a good dialyzer, a fair dialyzer, or a poor dialyzer and then display the category of the dialyzer on the screen for a user.

In some embodiments, instead of three categories, two categories or a pass/fail categorization may be employed by the HCT computer and display 35. The HCT computer and display 35 may compare the accumulated red blood volume obtained at step 508 with a pass-fail threshold, such that when the accumulated red blood volume exceeds the threshold, the dialyzer is categorized under the fail category and when the accumulated red blood volume is equal to or below the threshold, the dialyzer is categorized under the pass category. The HCT computer and display 35 may then provide a user with either a pass or a fail for the dialyzer under test.

In an exemplary implementation, dialyzer efficiency can be compared and categorized based on measured $\Delta R$ values instead of the accumulated red blood volume. A $\Delta R$ value at a designated time $t_m$ for each dialyzer being evaluated may be compared to one another. In some embodiments, a dialyzer with the lowest $\Delta R$ value at the designated time $t_m$ is the most efficient diaylzer. In some embodiments, the dialyzers are categorized as good, fair, and poor by comparing each dialyzer's $\Delta R$ value at the designated time $t_m$ with a first $\Delta R$ threshold and a second $\Delta R$ threshold. In some embodiments, the dialyzers are categorized as pass/fail by comparing each dialyzer's $\Delta R$ value at the designated time $t_m$ with a $\Delta R$ threshold.

Figure 6:
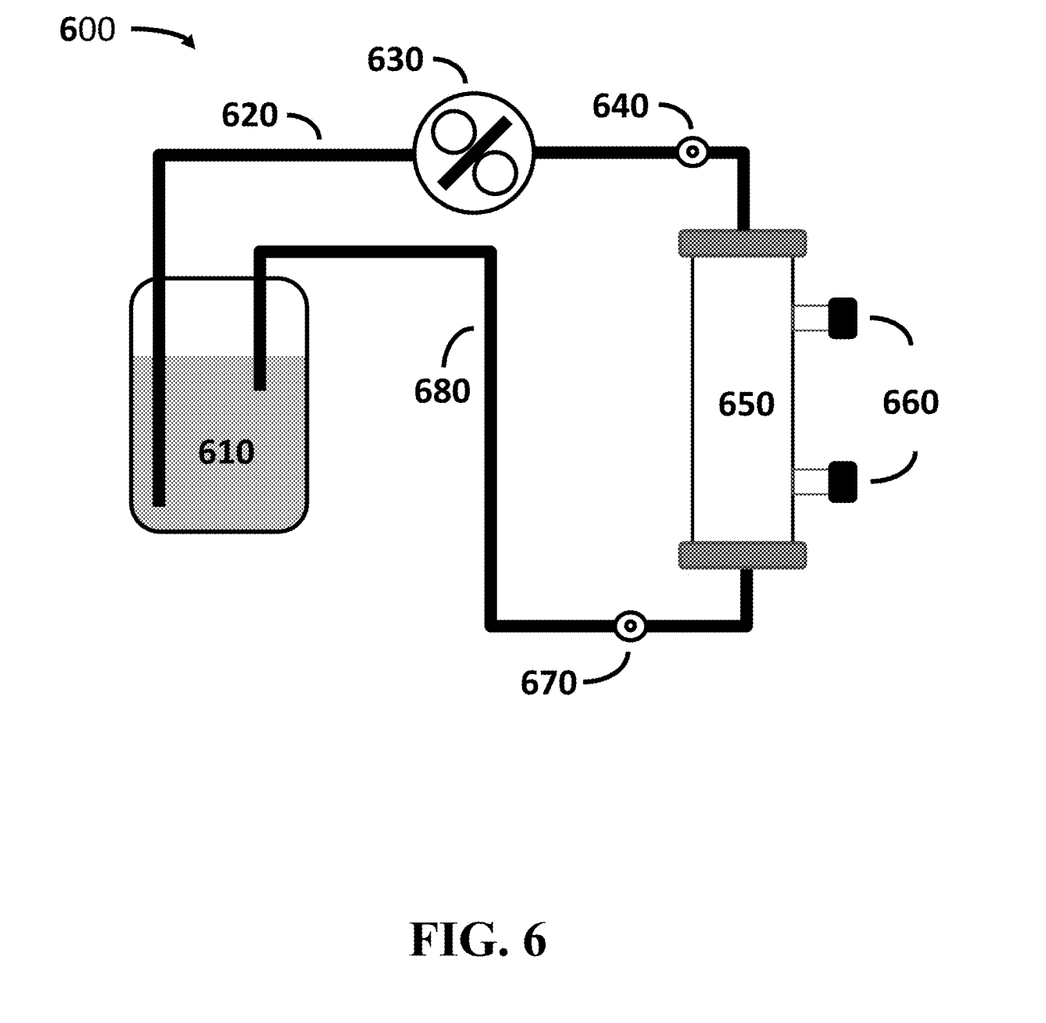
FIG. 6 illustrates a system configuration for determining accumulated red blood volume lost per unit time according to some embodiments of the disclosure.

An alternative system configuration 600 to measuring dialyzer efficiency is shown in FIG. 6. A dialyzer may be evaluated in-vitro using the system 600. The blood in the container 610 may be human blood of sufficient volume to fill the tubing set (620 and 680) and the dialyzer 650 with an equal amount or more of blood remaining in the container 610 while the blood is circulating. The blood may contain sufficient heparin added to ensure short-term clotting does not occur in stagnant blood samples. In some embodiments, bovine blood may be used in the test system configuration 600. In some embodiments, an in-vivo blood source from a patient is used.

In an initial step, the prepared blood in container 610 is pumped out of the container 610 through blood line 620 using the peristaltic pump 630. The blood arrives at the input side of the dialyzer 650 through tubing set 620 after the pump. At location 640, the blood line can be configured to contain a blood draw "button," which self-seals once a hypodermic needle is inserted and removed.

The dialyzer ports 660, which normally support dialysate flow, are blocked. As in the laboratory environment of FIG. 4, blocking these ports indicates that the UFR is 0, thus, when applying Eqs. 1-5, UFR is set to 0. The blood line 680 carries the blood from the dialyzer 650 back into the blood container 610. Another blood draw "button" 670 may be configured in the blood line 680 to support the drawing of blood samples that have passed through the dialyzer 650.

The flow rate $Q_{b\_in}$ may be set by the speed of pump 630. At timed intervals, a blood draw is performed, for example, 5 cc to 7 cc, by inserting a needle connected to a syringe into the "button" at 640 and pulling the syringe until the appropriate volume registers in the syringe markings. A separate syringe and needle is used to collect a similar sample from the output side of the dialyzer at the "button" 670. Blood sample in both syringes may then be immediately measured with a Coulter cell counter, or other cell counter device, to obtain the $HCT_{in}$ and $HCT_{out}$ values from the 640 "button" and the 670 "button", respectively.

With $Q_{b\_in}$, $HCT_{in}$, and $HCT_{out}$ determined, $\Delta R$ may be obtained using, for example, step 506 of FIG. 5, and accumulated $\Delta R$ may be obtained using step 508 of FIG. 5. The accumulated $\Delta R$ corresponds to the accumulated red blood cell volume or residual red blood cell volume in the dialyzer over an elapsed time.

In FIG. 6, the "buttons" at locations 640 and 670 can be replaced with other methods of drawing blood samples. For example, standard air traps for dialysis blood lines could be inserted in place of the "buttons." In this case, one of the ancillary small tubes attached to the air trap can be un-capped and the syringe connected to it. The air trap can be inverted and a blood sample removed by hypodermic suction of the syringe at location 640 for $HCT_{in}$ measurement and location 670 for $HCT_{out}$ measurement, respectively.

Using a cell counter may provide higher precision than other methods for determining the hematocrit values in the system 600. In some embodiments, approximations of the hematocrit values are possible by measuring hemoglobin instead. The hemoglobin measurements may then be used to approximate the hematocrit values. Hemoglobin measurements may incur some loss in precision compared to direct measurements of hematocrit. A quick conversion between measured hemoglobin numbers and hematocrit may be performed by multiplying the hemoglobin numbers by 3.0.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A system, comprising:
    a first sensor connected to a first portion of a blood flow path disposed on an input side of a dialyzer, wherein the first sensor is configured to obtain measurements relating to a characteristic of blood in the first portion of the blood flow path;
    a second sensor connected to a second portion of the blood flow path disposed on an output side of the dialyzer, wherein the second sensor is configured to obtain measurements relating to a characteristic of blood in the second portion of the blood flow path; and
    a controller configured to determine a red blood cell volume loss corresponding to an amount of red blood cells remaining in the dialyzer based on the measurements from the first and second sensors.

2. The system according to claim 1, wherein the measurements relating to the characteristic of the blood in the first portion of the blood flow path are hemoglobin measurements, and the measurements relating to the characteristic of the blood in the second portion of the blood flow path are hemoglobin measurements.

3. The system according to claim 1, wherein a flowrate of the blood in the first portion of the blood flow path is equal to a flowrate of the blood in the second portion of the blood flow path.

4. The system according to claim 1, wherein the controller is further configured to determine a flowrate of the blood in the first portion of the blood flow path;
    wherein determining the red blood cell volume loss is further based on the determined flowrate of the blood in the first portion of the blood flow path.

5. The system according to claim 4, wherein the flowrate of the blood in the first portion of the blood flow path is equal to a flowrate of the blood in the second portion of the blood flow path;
    wherein the controller is further configured to:
        determine an input red blood cell volume flow and an output red blood cell volume flow based on a measurement from the first sensor, a measurement from the second sensor, and the flowrate; and
        determine a difference $\Delta R$ between the input red blood cell volume flow and the output red blood cell volume flow; and
    wherein determining the red blood cell volume loss is further based on using one or more $\Delta R$ values over a period of time to determine an accumulated red blood cell volume loss value.

6. The system according to claim 4, wherein determining the flowrate of the blood in the first portion of the blood flow path is based on a pumping rate of a pump configured to pump the blood in the first portion of the blood flow path into the dialyzer.

7. The system according to claim 4, further comprising:
    a flowmeter coupled to the first portion of the blood flow path;
    wherein the controller is configured to determine the flowrate of the blood in the first portion of the blood flow path using the flowmeter.

8. The system according to claim 1, wherein the controller is further configured to:
    determine a flowrate of the blood in the first portion of the blood flow path;
    determine a flowrate of the blood in the second portion of the blood flow path;
    determine an input red blood cell volume flow corresponding to blood flowing into the dialyzer based on a measurement from the first sensor and the flowrate of the blood in the first portion of the blood flow path;
    determine an output red blood cell volume flow corresponding to blood flowing out of the dialyzer based on a measurement from the second sensor and the flowrate of the blood in the second portion of the blood flow path; and
    determine a difference $\Delta R$ between the input red blood cell volume flow and the output red blood cell volume flow; and
    wherein determining the red blood cell volume loss is further based on using one or more $\Delta R$ values over a period of time to determine an accumulated red blood cell volume loss value.

9. The system according to claim 8, wherein determining the flowrate of the blood in the second portion of the blood flow path is based on an ultrafiltration rate and the flowrate of the blood in the first portion of the blood flow path.

10. The system according to claim 1, wherein the controller is further configured to output a rating for the dialyzer based on the red blood cell volume loss.

11. The system according to claim 1, wherein the controller is further configured to output a comparison of the dialyzer to one or more other dialyzers based on respective red blood cell volume losses determined for each dialyzer.

12. The system according to claim 1, wherein the first and second sensors are hematocrit measurement devices.

13. A system, comprising:
    a first port disposed in a first portion of a blood flow path disposed on an input side of a dialyzer, wherein the first port is configured to permit blood to be drawn from the first portion of the blood flow path;
    a second port disposed in a second portion of the blood flow path disposed on an output side of the dialyzer, wherein the second port is configured to permit blood to be drawn from the second portion of the blood flow path; and
    a controller to determine a red blood cell volume loss corresponding to an amount of red blood cells remaining in the dialyzer based on measurements relating to a characteristic of blood in the first portion of the blood flow path and measurements relating to a characteristic of blood in the second portion of the blood flow path, wherein the measurements relating to the characteristic of the blood in the first portion of the blood flow path correspond to blood drawn from the first portion of the blood flow path, and wherein the measurements relating to the characteristic of the blood in the second portion of the blood flow path correspond to blood drawn from the second portion of the blood flow path.

14. The system according to claim 13, wherein the measurements relating to the characteristic of the blood in the first portion of the blood flow path are hemoglobin measurements, and the measurements relating to the characteristic of the blood in the second portion of the blood flow path are hemoglobin measurements.

15. The system according to claim 13, wherein the measurements relating to the characteristic of the blood in the first portion of the blood flow path are hematocrit measurements, and the measurements relating to the characteristic of the blood in the second portion of the blood flow path are hematocrit measurements.

16. The system according to claim 13, wherein a flowrate of the blood in the first portion of the blood flow path is equal to a flowrate of the blood in the second portion of the blood flow path.

17. The system according to claim 13, wherein the controller is further configured to: determine a flowrate of the blood in the first portion of the blood flow path; and wherein determining the red blood cell volume loss is further based on the determined flowrate of the blood in the first portion of the blood flow path.

18. The system according to claim 17, wherein the flowrate of the blood in the first portion of the blood flow path is equal to a flowrate of the blood in the second portion of the blood flow path;

wherein the controller is further configured to:
determine an input red blood cell volume flow and an output red blood cell volume flow based on a measurement corresponding to the blood in the first portion of the blood flow path, a measurement corresponding to the blood in the second portion of the blood flow path, and the flowrate; and
determine a difference $\Delta R$ between the input red blood cell volume flow and the output red blood cell volume flow; and wherein determining the red blood cell volume loss is further based on using one or more $\Delta R$ values over a period of time to determine an accumulated red blood cell volume loss value.

19. The system according to claim 17, wherein determining the flowrate of the blood in the first portion of the blood flow path is based on a pumping rate of a pump configured to pump the blood in the first portion of the blood flow path into the dialyzer.

20. The system according to claim 17, further comprising:
a flowmeter coupled to the first portion of the blood flow path;
wherein the controller is configured to determine the flowrate of the blood in the first portion of the blood flow path using the flowmeter.

21. The system according to claim 13, wherein the controller is further configured to output a rating for the dialyzer based on the red blood cell volume loss.

22. The system according to claim 13, wherein the controller is further configured to output a comparison of the dialyzer to one or more other dialyzers based on respective red blood cell volume losses determined for each dialyzer.

* * * * *